(12) United States Patent
Takanabe et al.

(10) Patent No.: US 6,228,378 B1
(45) Date of Patent: May 8, 2001

(54) COSMETIC COMPOSITION

(75) Inventors: Hidenobu Takanabe; Atsuyuki Kiba; Kenji Kodama, all of Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/148,694

(22) Filed: Sep. 4, 1998

(30) Foreign Application Priority Data

Dec. 8, 1997 (JP) .................................................... 9-337049
Dec. 8, 1997 (JP) .................................................... 9-337050

(51) Int. Cl.[7] .............................. A61K 6/00; A61K 7/00; A61K 7/135
(52) U.S. Cl. ............................................. 424/401; 424/62
(58) Field of Search ........................................ 424/401, 62

(56) References Cited

U.S. PATENT DOCUMENTS 5,976,555 * 11/1999 Liu et al. .............................. 424/401

FOREIGN PATENT DOCUMENTS 59-141512 * 8/1984 (JP) .
8-253408 10/1996 (JP) .

* cited by examiner

*Primary Examiner*—Thurman K. Page
*Assistant Examiner*—S. Howard
(74) *Attorney, Agent, or Firm*—Oblon, Spivak, McClelland, Maier & Neustadt, P.C.

(57) ABSTRACT

Disclosed herein is a cosmetic composition comprising carbon dioxide gas, wherein the viscosity of the cosmetic composition is 100 to 500,000 mPa.s at 25° C., and the concentration of the carbon dioxide gas in the cosmetic composition ejected from the container is kept at 60 ppm or more for 15 minutes after the ejection. The cosmetic composition has the ability to retain carbon dioxide gas therein, can sustain a blood circulation-facilitating effect, has the effect of improving dull looking skin, dark circles and uneven skin tone, and gives users a pleasant feeling upon use.

12 Claims, No Drawings

COSMETIC COMPOSITION

BACKGROUND OF THE INVENTION

1. Field of the Invention

The present invention relates to a cosmetic composition which has the ability to retain carbon dioxide gas therein, provides a blood circulation-facilitating effect, improves dull looking skin, dark circles and uneven skin tone, has no slimy feel, and gives users a pleasant feeling upon use.

2. Discussion Of The Background

Carbon dioxide gas is known to have a blood circulation-facilitating action. In the field of cosmetic compositions, there are known, for example, a cosmetic composition in which carbon dioxide gas is incorporated into a water-based cosmetic, and the mixture is hermetically packaged in a pressure container (Japanese Patent Application Laid-Open No 141512/1984) and an aerosol product in which a stock solution containing carbon dioxide gas is hermetically packaged in an inner bag of an aerosol container of dual structure (Japanese Patent Application Laid-Open No. 253408/1996). However, it is difficult for these cosmetic compositions to retain the carbon dioxide gas therein for a long period of time, and so the carbon dioxide gas is hard to keep on the skin upon use. As a result, the blood circulation-facilitating effect of the carbon dioxide gas can be neither sufficiently achieved nor sustained.

On the other hand there are cosmetic compositions in which a water-soluble thickener is incorporated for the purpose of improving their usability and stability. However, they have a slimy feel of their own when applied, and often give users an unpleasant feeling.

SUMMARY OF THE INVENTION

Accordingly, it is an object of the present invention to provide a cosmetic composition which has one or more of the ability to retain carbon dioxide gas therein, sustain a blood circulation-facilitating effect, improve dull looking skin, dark circles and uneven skin tone, have no slimy feel, and give users a pleasant feeling upon use.

The present inventors have now provided such a cosmetic composition, which has a specific viscosity and which contains at least a fixed amount of carbon dioxide gas even after the lapse of time. This composition has the ability to retain carbon dioxide therein, can sustain a blood circulation-facilitating effect, has no slimy feel and gives users a refreshed, pleasant feeling upon use.

According to the present invention, there is thus provided a cosmetic composition comprising carbon dioxide gas, wherein the viscosity of the cosmetic composition is 100 to 500,000 mPa.s at 25° C., and preferably wherein the concentration of carbon dioxide gas in the cosmetic composition at room temperature and standard pressure is kept at 60 ppm or more for at least 15 minutes after ejection from, for example, a pressurized container.

DETAILED DESCRIPTION OF THE PREFERRED EMBODIMENTS

In the cosmetic composition according to the present invention., carbon dioxide gas is incorporated in a state dissolved in a water-based cosmetic composition. It is preferable that the concentration of the carbon dioxide gas in the cosmetic composition, when ejected from a (pressurized) container, be kept at 60 ppm or more, preferably 100 to 20,000 ppm, particularly preferably 200 to 10,000 ppm, each for 15 minutes or more after the ejection.

It is known that carbon dioxide gas develops a vasodilator action in the case where the pH of a solution, in which the carbon dioxide gas is dissolved, is acidic. Accordingly, it is preferred that the pH of the cosmetic composition be adjusted to not higher than 7, particularly 5 to 6.5. When carbon dioxide gas is incorporated under pressure into a cosmetic composition and dissolved therein, the pH of the cosmetic composition comes to show a stronger acidity. Therefore, it is preferable to adjust the pH of the cosmetic composition in such a manner that the final pH thereof falls within the above range. This is within the skill of the ordinary artisan. Examples of pH adjusters include organic acids such as citric acid and tartaric acid, salts thereof, and phosphoric acid and salts thereof.

The cosmetic composition according to the present invention has a viscosity of 100 to 500,000 mPa.s, preferably 200 to 200,000 mPa.s, particularly preferably 500 to 20,000 mPa.s to 25° C. This viscosity enhances the ability to retain carbon dioxide gas therein and gives a pleasant feeling upon use.

In the present invention, a thickener is used to make the viscosity of the cosmetic composition the stated viscosity. Examples thereof include synthetic polymers such as carboxyvinyl polymers, acrylic acid-alkyl methacrylate copolymers, polyvinyl alcohol, sodium polyacrylate, polyvinyl pyrrolidone and polyethylene glycol; semisynthetic polymers such as methyl cellulose, ethyl cellulose, hydroxyethyl cellulose, hydroxypropyl cellulose, carboxymethyl cellulose, methylhydroxypropyl cellulose, soluble starch and propylene glycol alginate; natural polymers such as sodium alginate, chitin and derivatives thereof, chitosan and derivatives thereof, pullulan, guar gum, locust bean gum, quince seed, carrageenans, galactan, gum arabic, tragacanth gum, pectin, mannan, starch, xanthan gum, dextran, succinoglucan, curdlan, gelatin, casein, albumin, and collagen; and water-swellable clay minerals such as montmorillonite, beidellite, nontronite,hectorite, saponite and stevenllite.

Among them, water-soluble thickeners, for example, carrageenans such as lambda carrageenan, kappa carrageenan, xanthan gum, sodium alginate, carboxyvinyl polymers, polyvinyl pyrrolidone, chitin and derivatives thereof, chitosan and derivatives thereof, and pullulan are preferred, with carrageenans, xanthan gum, sodium alginate and carboxyvinyl polymers being particularly preferred.

The thickener used in the present invention preferably has a film strength of at least $6.0 \times 10^4$ g/cm$^2$, particularly $10.0 \times 10^4$ to $30.0 \times 10^4$ g/cm$^2$ as measured in the following manner, from the viewpoint of the ability to retain carbon dioxide gas. Namely, 1 wt. % of a thickener is added to an aqueous base solution having the following composition, the solution being casted in a mold to form a film 50 μm thick by 20 mm long by 100 mm wide after standing for 15 hours under conditions of 25° C. and 40% RH. Thereafter, the film-strength is measured, under the same conditions of 25° C. and 40 RH, by means of a Tensilon film strength meter, UCT-100W (manufactured by ORIENTEC CO.).

| (Aqueous base solution) | (wt. %) |
|---|---|
| Polyvinyl alcohol (Gohsenol EG, product of The Nippon Synthetic Chemical Industry Co., Ltd.) | 8.0 |
| 1,3-Butylene glycol | 3.0 |
| Purified water | Balance |
| Total | 100.0 |

These thickeners may be used either singly or in any combination thereof so far as the viscosity within the range described above can be attained. For example, the thickener is incorporated in an amount of 0.01 to 10 wt. %, preferably 0.1 to 3 wt. %, particularly preferably 0.3 to 2 At. %, based on the total weight of the composition.

When a whitening agent is incorporated into the cosmetic composition according to the present invention, the effect of improving dull looking skin, dark circles and uneven skin tone and the like of the skin is markedly enhanced by the synergistic effect of the whitening agent and the carbon dioxide gas.

Examples of the whitening agent include ascorbic acid and derivatives thereof, hydroquinone derivatives, kojic acid and derivatives thereof, animal placenta extracts and plant extracts.

Specifically, examples of the derivatives of ascorbic acid include salts of L-ascorbic acid phosphate, salts of L-ascorbic acid phosphate, salts of L-ascorbic acid sulfate and salts of L-ascorbic acid. The salts include salts with monovalent to trivalent metals such as Na, K, Ca, Mg and Al.

Examples of the hydroquinone derivatives include condensates of hydroquinone or an alkylhydroquinone with a saccharide, such as arbutin.

Examples of the derivatives of kojic acid include kojic acid monobutyrate, kojic acid monocaprate, kojic acid monostearate, kojic acid monocinnamate, kojic acid monobenzoate, kojic acid dibutyrate, kojic acid dipalmitate, kojic acid distearate and kojic acid dioleate.

The animal placenta extracts include those extracted from placenta of mammal in accordance with a method known per se in the art, for example, placenta extracts generally marketed as water-soluble placenta extracts.

Examples of the plant extracts include extracts from plants such as tea, puerariae root, clove, licorice, loquat, spruce, ginseng, Chinese peony, Nippon hawthorn, ophiopogon tuber, ginger, pine, mulberry bark, sweet grass, artemisia capillaris, catechu, pothos vine, chamomile, althea, Japanese spiraea, water-cress, quinine tree, common comfrey, rosemary and scopolia rhizome.

Of these, the plant extracts are preferred, with the extracts from tea, chamomile, puerariae root, althea, clove and loquat being particularly preferred.

These whitening agents may be used either singularly or in any combination thereof and are preferably incorporated in an amount of 0.01 to 10 wt. %, more preferably 0.1 to 5 wt. %, particularly preferably 0.1 to 3 wt. % based on the total weight of the composition. In the present invention, the amount is expressed in terms of dry solids content where a plant extract is used.

The cosmetic composition of the present invention can be manufactured by dissolving or dispersing said thickeners, whitening agents and other ingredients in an aqueous medium and further by incorporating $CO_2$ gas.

In order to stably retain the carbon dioxide gas, the cosmetic composition according to the present invention is preferably provided as an unself-propelling type product which is hermetically packaged in a pressure container. As a method for doing so, there is adopted, for example, a method in which a cosmetic composition is charged into a pressure container, and carbon dioxide gas or a mixed gas containing it is hermetically packaged therein; a method in which a cosmetic composition containing a carbonate such as sodium hydrogencarbonate is charged into a pressure container, a pH adjuster is added thereto to generate carbon dioxide gas, and the container is immediately sealed; or a method in which a cosmetic composition and solid carbon dioxide pellets are charged into a pressure container, and the container is immediately sealed. Of these, the method of hermetically packaging the high-pressure gas in the container is particularly preferred.

According to such a method, a part of carbon dioxide gas is incorporated in a state dissolved in the cosmetic composition, the remainder is present as a gas state in the container. The amount of the carbon dioxide gas incorporated may be adjusted by changing the amount of the carbon dioxide gas charged.

No particular limitation is imposed on the pressure container used in the present invention so far as it withstands the pressure described above until the composition is consumed after preparation, and can hermetically hold the cosmetic composition therein. For example, a metal container made of aluminum or tin plate, a synthetic resin container made of an acetal resin or polycarbonate resin, or a glass container is used.

In the present invention, it is preferred that a container of dual structure be used as the pressure container. For example, a pressure container having an inner bag made of a resin in an outer container may be used as the container of dual structure. When such a container is used, the cosmetic composition according to the present invention is hermetically packaged in the inner bag, and a pressurizing gas is hermetically packaged in between the outer container and said inner bag. Examples of the outer container include the same containers as described above. Examples of the resin used for the inner bag include polyethylene, nylon and ethylene vinyl alcohol copolymers. These resins may be used as a single-layer structure or laminated structure. At least two of these resins may be blended, or aluminum may be partially used. As the pressurizing gas hermetically packaged in the outer container, liquefied petroleum gas (LPG), dimethyl ether, nitrogen, carbon dioxide gas, flon and the like may be used either singly or in any combination thereof. The pressure of the gas at 25° C. may be optional so far as the liquid within the inner bag can be propelled thereby. However, it may be preferably 0.1 to 1.0 MPa, more preferably 0.3 to 0.95 MPa. In particular, it is preferred that carbon dioxide gas or a mixed gas containing it exists outside the inner bag (within the outer container), since the carbon dioxide gas permeates through the inner bag to be supplied to the cosmetic composition, whereby the concentration of the carbon dioxide gas in the cosmetic composition can be kept high. In this case, it is preferred that polyethylene be used for the inner bag.

The cosmetic composition according to the present invention hermetically packaged in the container of dual structure is produced by, for example, charging the cosmetic composition (which may or may not contain carbon dioxide gas) into the inner bag, introducing a pressurizing gas containing carbon dioxide gas under pressure outside the inner bag, sealing the outer container and then aging the composition. By this aging, the carbon dioxide gas introduced under pressure outside the inner bag permeates through within the inner bag and is dissolved in the cosmetic composition. In general, a week at room temperature will suffice for such aging. Such a period can be shorted by heating.

In the cosmetic composition according to the present invention, ingredients commonly used in classical cosmetic compositions may be suitably incorporated in addition to the above-described components so far as no detrimental influence is thereby imposed on the effects of the present invention. Such are determinable by those of ordinary skill.

The cosmetic composition according to the present invention may be formulated in any form of toilet water, cosmetic emulsion, hair lotion, hair tonic, shampoo, and the like.

EXAMPLES

Example 1

Cosmetic compositions of the corresponding formulations shown in Tables 1 and 2 were prepared by dissolving the prescribed components in water and hermetically packaged in pressure containers to obtain cosmetic products. The thus-obtained cosmetic products were evaluated as to a feeling upon use and the ability to retain carbon dioxide gas. The results are shown collectively in Tables 1 and 2.

<Evaluation Methods>

(1) Feeling upon use:

A proper amount (0.5 to 1 g to the whole face) of a sample cosmetic composition was applied to the face of each of ten expert panelists, thereby organoleptically evaluating the composition as to a feeling upon use (whether it gave the panelists a refreshed feeling and had a slimy feel) right after the application in accordance with the following standard:

○: At least seven panelists judged to be good;

Δ: Four to six panelists judged to be good;

X: At most three panelists judged to be good.

(2) The ability to retain carbon dioxide gas:

The concentration of carbon dioxide gas in a sample cosmetic composition within 3 minutes from its ejection from the pressure container at room temperature and standard pressure (25° C., 1013 hPa) and the concentration of the carbon dioxide gas 15 minutes after the ejection were measured by an ion analyzer EA940 (manufactured by ORION CO.) to compare the concentration exiting with the concentration after 15 minutes, thereby evaluating the cosmetic composition as to the ability to retain carbon dioxide gas in accordance with the following standards:

⊚: Carbon dioxide gas was retained by at least 85% after 15 minutes;

○: Carbon dioxide gas was retained by at least 70% after 15 minutes;

Δ: Carbon dioxide gas was retained by at least 30% but not lower than 70% after 15 minutes;

X: Carbon dioxide gas was retained by lower than 30% after 15 minutes.

TABLE 1

| Component (wt. %) | Invention product | | | | |
|---|---|---|---|---|---|
| | 1 | 2 | 3 | 4 | 5 |
| Purified water | Bal. | Bal. | Bal. | Bal. | Bal. |
| Ethanol | — | — | — | — | — |
| 1,3-Butylene glycol | 2.00 | 2.00 | 2.00 | 2.00 | 2.00 |
| Glycerol | 2.00 | 2.00 | 2.00 | 2.00 | 2.00 |
| Perfume base | 0.10 | 0.10 | 0.10 | 0.10 | 0.10 |
| Antiseptic | q.s. | q.s. | q.s. | q.s | q.s. |
| Polyoxyethylene lauryl ether (20 E.O.) | 0.50 | 0.50 | 0.50 | 0.50 | 0.50 |
| Succinic acid | 0.30 | 0.30 | 0.30 | 0.30 | 0.30 |
| Disodium hydrogenphosphate | 0.50 | 0.50 | 0.50 | 0.50 | 0.50 |
| Carboxyvinyl polymer (film strength: $12.5 \times 10^4$ g/cm$^2$) | 0.80 | — | — | — | 0.40 |
| Carrageenan (film strength: $14.0 \times 10^4$ g/cm$^2$) | — | 0.80 | — | — | — |
| Xanthan gum (film strength: $14.5 \times 10^4$ g/cm$^2$) | — | — | 0.80 | — | — |
| Polyvinyl pyrrolidone (film strength: $13.0 \times 10^4$ g/cm$^2$) | — | — | — | 0.80 | — |
| Amount of carbon dioxide gas incorporated (ppm) | 1000 | 1000 | 1000 | 1000 | 1000 |
| Viscosity (mPa · s) | 8500 | 5000 | 200 | 100 | 500 |
| Feeling upon use | ○ | ○ | ○ | ○ | ○ |
| Ability to retain carbon dioxide gas | ⊚ | ⊚ | ○ | ○ | ⊚ |

TABLE 2

| Component (wt. %) | Comparative product | | |
|---|---|---|---|
| | 1 | 2 | 3 |
| Purified water | Bal. | Bal. | Bal. |
| Ethanol | — | — | 10.0 |
| 1,3-Butylene glycol | 2.00 | 2.00 | 2.00 |
| Glycerol | 2.00 | 2.00 | 2.00 |
| Perfume base | 0.10 | 0.10 | 0.10 |
| Antiseptic | q.s. | q.s. | q.s. |
| Polyoxyethylene lauryl ether (20 E.O.) | 0.50 | 0.50 | 0.50 |
| Succinic acid | 0.30 | 0.30 | 0.30 |
| Disodium hydrogenphosphate | 0.50 | 0.50 | 0.50 |
| Carboxyvinyl polymer (film strength: $12.5 \times 10^4$ g/cm$^2$) | — | 0.80 | 0.80 |
| Carrageenan (film strength: $14.0 \times 10^4$ g/cm$^2$) | — | — | — |
| Xanthan gum (film strength: $14.5 \times 10^4$ g/cm$^2$) | — | — | — |
| Polyvinyl pyrrolidone (film strength: $13.0 \times 10^4$ g/cm$^2$) | — | — | — |
| Amount of carbon dioxide gas incorporated (ppm) | 1000 | 10 | 10 |
| Viscosity (mPa · s) | 25 | 5000 | 4000 |
| Feeling upon use | Δ | x | x |
| Ability to retain carbon dioxide gas | x | x | x |

Example 2

Cosmetic compositions of their corresponding formulations shown in Table 3 were prepared as per Example 1 and hermetically packaged in pressure containers to obtain cosmetic products. The thus-obtained cosmetic products were evaluated as to a feeling upon use in the same manner as in Example 1 and the effect of improving skin dinginess in the following manner. The results are shown collectively in Table 3.

<Evaluation Methods>

A proper amount of a sample cosmetic composition was applied to the face of each of ten persons, who suffered from skin dinginess, once or twice a day for 2 weeks, thereby organoleptically evaluating the composition as to the effect of improving skin dinginess in comparison with the condition before use in accordance with the following standard:

○: At least seven persons felt skin dinginess being improved;

Δ: Four to six persons felt skin dinginess being improved;

X: At most three persons felt skin dinginess being improved.

TABLE 3

|  | Invention product | | | | | | | | |
| --- | --- | --- | --- | --- | --- | --- | --- | --- | --- |
| Component (wt. %) | 5 | 6 | 7 | 8 | 9 | 10 | 11 | 12 | 13 |
| Purified water | Bal. | Bal. | Bal. | Bal. | Bal. | Bal. | Bal. | Bal. | Bal. |
| Ethanol | — | — | — | — | — | — | 10.0 | — | — |
| 1,3-Butylene glycol | 2.00 | 2.00 | 2.00 | 2.00 | 2.00 | 2.00 | 2.00 | 2.00 | 2.00 |
| Glycerol | 2.00 | 2.00 | 2.00 | 2.00 | 2.00 | 2.00 | 2.00 | 2.00 | 2.00 |
| Perfume base | 0.10 | 0.10 | 0.10 | 0.10 | 0.10 | 0.10 | 0.10 | 0.10 | 0.10 |
| Antiseptic | q.s. | q.s. | q.s. | q.s. | q.s. | q.s. | q.s. | q.s. | q.s. |
| Polyoxyethylene lauryl ether (20 E.O.) | 0.50 | 0.50 | 0.50 | 0.50 | 0.50 | 0.50 | 0.50 | 0.50 | 0.50 |
| Succinic acid | 0.30 | 0.30 | 0.30 | 0.30 | 0.30 | 0.30 | 0.30 | 0.30 | 0.30 |
| Disodium hydrogenphosphate | 0.50 | 0.50 | 0.50 | 0.50 | 0.50 | 0.50 | 0.50 | 0.50 | 0.50 |
| Carboxyvinyl polymer (film strength: $12.5 \times 10^4$ g/cm$^2$) | 0.80 | 0.80 | 0.80 | 0.80 | 0.80 | 0.80 | 0.80 | 0.80 | 0.80 |
| Chamomile extract | 0.80 | — | — | — | — | — | 0.80 | 0.40 | 0.40 |
| Puerariae root extract | — | 0.80 | — | — | — | — | — | 0.40 | — |
| L-Ascorbic acid | — | — | 0.80 | — | — | — | — | — | — |
| Kojic acid | — | — | — | 0.80 | — | — | — | — | 0.40 |
| Amount of carbon dioxide gas incorporated (ppm) | 1000 | 1000 | 1000 | 1000 | 1000 | 5000 | 1000 | 5000 | 1000 |
| Viscosity (mPa.s) | 5000 | 5000 | 5000 | 5000 | 5000 | 5000 | 5000 | 5000 | 5000 |
| Feeling upon use | ○ | ○ | ○ | ○ | ○ | ○ | ○ | ○ | ○ |
| Effect of improving skin dinginess | ○ | ○ | ○ | ○ | Δ | Δ | ○ | ○ | ○ |

Example 3

Cosmetic compositions of their corresponding formulations shown in Table 4 were prepared as per Example 1 and hermetically packaged in pressure containers of dual structure to obtain cosmetic products. The production was conducted by charging each composition into an inner bag of the container of dual structure and introducing a gas containing carbon dioxide gas under pressure between an outer container and the inner bag. The cosmetic products thus obtained contained the carbon dioxide gas at the desired concentration.

TABLE 4

|  | Invention product | |
| --- | --- | --- |
| Component (wt. %) | 14 | 15 |
| Purified water | Balance | Balance |
| Ethanol | — | — |
| Glycerol | 2.00 | 2.00 |
| Perfume base | 0.10 | 0.10 |
| Antiseptic | q.s. | q.s. |
| Succinic acid | 0.30 | 0.30 |
| Disodium hydrogenphosphate | 0.50 | 0.50 |
| Carboxyvinyl polymer | 0.80 | 0.80 |
| Chamomile extract | 0.80 | 0.80 |
| Material for inner bag | Low density polyethylene | Low density polyethylene |
| Material for outer container | Aluminum | Aluminum |
| Composition of gas (wt. %/wt. %) | $N_2/CO_2$ 50/50 | $CO_2$ only — |
| Initial pressure | 0.9 MPa | 0.9 MPa |
| Concentration of carbon dioxide gas (3 minutes after ejection) | 3000 ppm | 5000 ppm |
| Ability to retain carbon dioxide gas | ⊚ | ⊚ |
| Viscosity (25° C. ,mPa · s) | 20,000 | 20,000 |

Based on the above, one of ordinary skill in the art can prepare compositions according to the invention having the desired amount of carbon dioxide upon ejection from a pressure container and 15 minutes thereafter at room temperature and standard pressure.

Japanese patent applications 9-337049 and 9-337050, both filed Dec. 8, 1997, are hereby incorporated herein by reference.

What is claimed is:

1. A cosmetic composition having a viscosity in the range of 100 to 500,000 mPa.s at 25° C. comprising:

carbon dioxide gas, a thickener selected from the group consisting of a synthetic polymer, a semisynthetic polymer, a natural polymer and water-swellable clay, and water, wherein said composition retains carbon dioxide at a concentration of at least 60 ppm or more for at least 15 minutes after release from a sealed, pressurized container.

2. The composition of claim 1, wherein said thickener has a film strength of at least $6.0 \times 10^4$ g/cm$^2$.

3. The composition of claim 1, which has a viscosity of at least 500 mPa.s.

4. The composition of claim 1, which is water-based.

5. A container of dual structure comprising:

an inner bag containing the composition of claims 1 and an outer container.

6. The container of claim 5, wherein a pressurizing gas is charged hermetically between the inner bag and the outer container.

7. The container of claim 6, wherein the pressurizing gas is selected from the group consisting of liquified petroleum gas, dimethyl ether, nitrogen and flon.

8. The container of claim 6, wherein the pressurizing gas comprises carbon dioxide.

9. The container of claim 5, wherein said inner bag is made of a carbon dioxide gas-permeable resin.

10. A method of stimulating blood circulation, comprising contacting the skin with the composition of claim 1 for a time and under conditions suitable for stimulating blood circulation.

11. A method for improving dull looking skin or reducing dark circles or uneven skin tone comprising contacting the skin with the composition of claim 1 for a time and under conditions suitable for improving dull looking skin or reducing dark circles or uneven skin tone.

12. The composition of claim 1, further comprising a whitening agent.

* * * * *